US009440902B2

(12) United States Patent
You et al.

(10) Patent No.: US 9,440,902 B2
(45) Date of Patent: Sep. 13, 2016

(54) METHOD FOR PRODUCING CARBONYL COMPOUND

(71) Applicant: CHIYODA CORPORATION, Yokohama-shi, Kanagawa (JP)

(72) Inventors: Zhixiong You, Yokohama (JP); Yoichi Umehara, Yokohama (JP); Tetsuro Matsumura, Yokohama (JP); Takeshi Minami, Yokohama (JP)

(73) Assignee: CHIYODA CORPORATION, Yokohama-shi (JP)

( * ) Notice: Subject to any disclaimer, the term of this patent is extended or adjusted under 35 U.S.C. 154(b) by 0 days.

(21) Appl. No.: 14/896,286

(22) PCT Filed: Jun. 3, 2014

(86) PCT No.: PCT/JP2014/002944
§ 371 (c)(1),
(2) Date: Dec. 4, 2015

(87) PCT Pub. No.: WO2014/196190
PCT Pub. Date: Dec. 11, 2014

(65) Prior Publication Data
US 2016/0130207 A1   May 12, 2016

(30) Foreign Application Priority Data
Jun. 5, 2013  (JP) ................................. 2013-119046

(51) Int. Cl.
*C07C 51/12* (2006.01)
*B01J 31/18* (2006.01)

(52) U.S. Cl.
CPC .............. *C07C 51/12* (2013.01); *B01J 31/181* (2013.01); *B01J 2231/321* (2013.01); *B01J 2531/821* (2013.01)

(58) Field of Classification Search
CPC ............................... C07C 51/12; B01J 31/181
USPC ....................................................... 562/519
See application file for complete search history.

(56) References Cited

U.S. PATENT DOCUMENTS

| 6,627,770 B1 | 9/2003 | Cheung et al. |
| 2012/0283471 A1 | 11/2012 | Torrence et al. |

FOREIGN PATENT DOCUMENTS

| JP | 47-3334 B | 1/1972 |
| JP | 63-253047 A | 10/1988 |
| JP | 9-235250 A | 9/1997 |
| JP | 2004-35433 A | 2/2004 |
| WO | 2004-506704 A | 3/2004 |

OTHER PUBLICATIONS

International Search Report dated Sep. 2, 2014, issued in counterpart Application No. PCT/JP2014/002944 (2 pages).
Notification of Transmittal of Translation of the International Preliminary Report on Patentability (Form PCT/IB/338) issued in counterpart International Application No. PCT/JP2014/002944 mailed Dec. 17, 2015 with Forms PCT/IB/373 and PCT/ISA/237 (11 pages).

*Primary Examiner* — Sikarl Witherspoon
(74) *Attorney, Agent, or Firm* — Westerman, Hattori, Daniels & Adrian, LLP

(57) ABSTRACT

To provide a production method for suppressing the reduction in production rate of a carbonyl compound due to transferring a noble metal component into liquid phase. A method for producing a carbonyl compound, including: a reaction step of reacting a carbonylation raw material with CO in liquid phase including a solid catalyst having noble metal complex on a resin carrier containing quaternized nitrogen to produce a carbonyl compound; a distillation step of distilling a reaction product liquid to recover gas phase distillate including the carbonyl compound; and a circulation step of circulating a bottom product from the distillation to reaction step. After part of the bottom product contacts with an acidic cation-exchange resin to remove nitrogen compound, liquid having higher moisture concentration than the bottom product contacts with the resin to extract noble metal complex captured by oligomer adsorbing the resin, and the complex is returned to the reaction step.

9 Claims, 2 Drawing Sheets

METHOD FOR PRODUCING CARBONYL COMPOUND

TECHNICAL FIELD

The present invention relates to a method for producing a carbonyl compound. In particular, the present invention relates to a method for producing acetic acid by a carbonylation reaction of methanol.

BACKGROUND ART

A method for reacting methanol and carbon monoxide in the presence of a noble metal catalyst to produce acetic acid is well known as a so-called "Monsanto's method". At first, this method has been developed as a method by a homogeneous catalytic reaction in which methanol and carbon monoxide are reacted in a reaction liquid including a rhodium compound as a metal catalyst and methyl iodide as a reaction accelerator dissolved in an acetic acid solvent including water (for example, PTL 1). Thereafter as a modified method thereof, a method by a heterogeneous catalytic reaction in which a solid catalyst having a rhodium compound supported thereon is used has been developed (for example, PTL 2).

In the production process by the homogeneous catalytic reaction, the solubility of the metal catalyst into the solvent is low and therefore the reaction rate cannot be increased, thereby resulting in the increase in size of a reactor. In addition, in order to achieve the increases in reaction rate and acetic acid selectivity, and to prevent the dissolved catalyst from being precipitated, moisture is required to be present in the reaction liquid in a relatively high concentration. The moisture, however, has the problem of resulting in the hydrolysis of methyl iodide used as a reaction accelerator to cause the reduction in yield of acetic acid and the corrosion of an apparatus. Therefore, the production process by the heterogeneous catalytic reaction less causing such a problem has been developed.

Carbonylation of methanol by the heterogeneous catalytic reaction is usually a procedure in which methanol and carbon monoxide are reacted using acetic acid as a solvent in the presence of a solid catalyst having a rhodium compound supported thereon and methyl iodide as a reaction accelerator in a reactor under heat and pressure. A reaction product liquid discharged from the reactor is guided to a separation system including a unit for distillation or the like, the produced acetic acid is separated and recovered, and the remaining liquid after separation is returned to the reactor. The inside of the reactor herein is a two-phase system in which solid catalyst particles are included in the reaction liquid including acetic acid, methanol, methyl iodide and the like (more specifically, three-phase system further including carbon monoxide gas bubbles), namely, a heterogeneous system. Herein, the reaction liquid also includes methyl acetate, dimethyl ether, hydrogen iodide, water and the like as reaction by-products in addition to the above components. As the solid catalyst, a catalyst having a rhodium complex supported on an insoluble resin particle including a pyridine ring in a molecular structure is usually used.

The solid catalyst is in the form where a basic nitrogen atom included in the pyridine ring in a resin carrier is quaternized by an alkyl iodide and a rhodium complex ion $[Rh(CO)_2I_2]^-$ is adsorbed thereto in an ion-exchange manner. Such an ion-exchange equilibrium highly shifts to the adsorption side and substantially hardly causes the rhodium complex ion to be desorbed from the resin carrier even if acetate ions and iodine ions are present in the liquid phase in the reactor, but a problem is that when the production of acetic acid is continued for a long time, a rhodium component is gradually transferred into the liquid phase. If the amount of the rhodium component transferred into the liquid phase is large to such an extent that is unignorable, such a disadvantage that rhodium is precipitated in a flasher, contained in mist, or is incorporated to a purge flow from the process is caused, and rhodium is lost in the reactor to result in the deterioration in catalyst function, leading to the reduction in reaction rate. Furthermore, the loss of expensive rhodium results in not only the reduction in productivity but also a significant increase in catalyst cost, causing the economic efficiency of the process to be remarkably impaired.

The reason why rhodium is transferred into the liquid phase is that the pyridine ring is decomposed and desorbed from the resin carrier during the production of acetic acid for a long time to cause rhodium to be transferred into the liquid phase. That is, since the rhodium complex ion and a quaternized nitrogen atom of the pyridine ring are under an ion-exchange equilibrium and the quaternized nitrogen atom is high in affinity to the rhodium complex ion, the rhodium complex ion is not easily desorbed from the resin carrier even if other negative ions are present. If the pyridine ring is present in the liquid phase, however, a part of the rhodium complex ion supported on the resin carrier may be adsorbed to the quaternized nitrogen atom of the pyridine ring in the liquid phase to be left from the resin carrier.

In order to inhibit the rhodium component from being thus transferred into the liquid phase, a method for decreasing the concentration of a pyridine ring in a liquid phase is provided as disclosed in PTL 3. In the method in PTL 3 in which a solid catalyst having rhodium immobilized to a quaternized pyridine resin is used to produce acetic acid from methanol and carbon monoxide, a pyridine ring-containing nitrogen compound produced by decomposition of the resin can be adsorbed to a cation exchanger to be removed, thereby inhibiting the rhodium component of the solid catalyst from being flown out to the liquid phase.

CITATION LIST

Patent Literature

PTL 1: Japanese Patent Publication No. S47-3334
PTL 2: Japanese Patent Application Laid-Open No. S63-253047
PTL 3: Japanese Patent Application Laid-Open No. 2004-35433

SUMMARY OF INVENTION

Technical Problem

While the method in PTL 3 is useful in terms of inhibiting the rhodium component from being flown out to the liquid phase, it has been found that the carbonylation reaction rate is reduced in comparison of the reaction rate before an operation for a long time with the reaction rate after the operation. The reason for this is because the nitrogen compound produced by decomposition of the resin includes an oligomer having two or more pyridine groups in an extremely slight amount and the oligomer is also adsorbed to the cation exchanger. Herein, a free pyridine group that is not bound to the cation exchanger is present in the oligomer, and captures the rhodium complex ion dissolved in an equilibrium manner or desorbed from a monomer adsorbed to the cation exchanger. Since the oligomer adsorbed to the cation exchanger is accumulated over time, the operation for a long time results in the reduction in rhodium component concentration in the reactor and the reduction in carbonylation reaction rate.

The present invention has been made under the above circumstances, and an object thereof is to provide a further effective production method for suppressing the reduction in production rate of a carbonyl compound due to transferring of a noble metal component such as rhodium into a liquid phase.

Solution to Problem

One aspect of the present invention provides a method for producing a carbonyl compound, including: a reaction step of reacting a carbonylation raw material with carbon monoxide in a liquid phase including a solid catalyst having a noble metal complex supported on a resin carrier containing quaternized nitrogen to produce a carbonyl compound; a distillation step of distilling a reaction product liquid from the reaction step to recover a gas phase distillate including the carbonyl compound; and a circulation step of circulating a bottom product from the distillation step to the reaction step, wherein, after at least a part of the bottom product is brought into contact with an acidic cation-exchange resin to remove a nitrogen compound included in the bottom product, a liquid having a higher moisture concentration than the bottom product is brought into contact with the acidic cation-exchange resin to extract a noble metal complex captured by an oligomer adsorbed to the acidic cation-exchange resin, and the extracted noble metal complex is returned to the reaction step.

DESCRIPTION OF EMBODIMENTS

Hereinafter, an embodiment of the method for producing a carbonyl compound of the present invention is specifically described. The present invention, however, is not limited to the following embodiment.

The method for producing a carbonyl compound of the present invention is, as described above, a method for producing a carbonyl compound, including: a reaction step of reacting a carbonylation raw material with carbon monoxide in a liquid phase including a solid catalyst having a noble metal complex supported on a resin carrier containing quaternized nitrogen to produce a carbonyl compound; a distillation step of distilling a reaction product liquid from the reaction step to recover a gas phase distillate including the carbonyl compound; and a circulation step of circulating a bottom product from the distillation step to the reaction step, in which, after at least a part of the bottom product is brought into contact with an acidic cation-exchange resin to remove a nitrogen compound included in the bottom product, a liquid having a higher moisture concentration than the bottom product is brought into contact with the acidic cation-exchange resin to extract a noble metal complex captured by an oligomer adsorbed to the acidic cation-exchange resin, and the extracted noble metal complex is returned to the reaction step.

Figure 1:
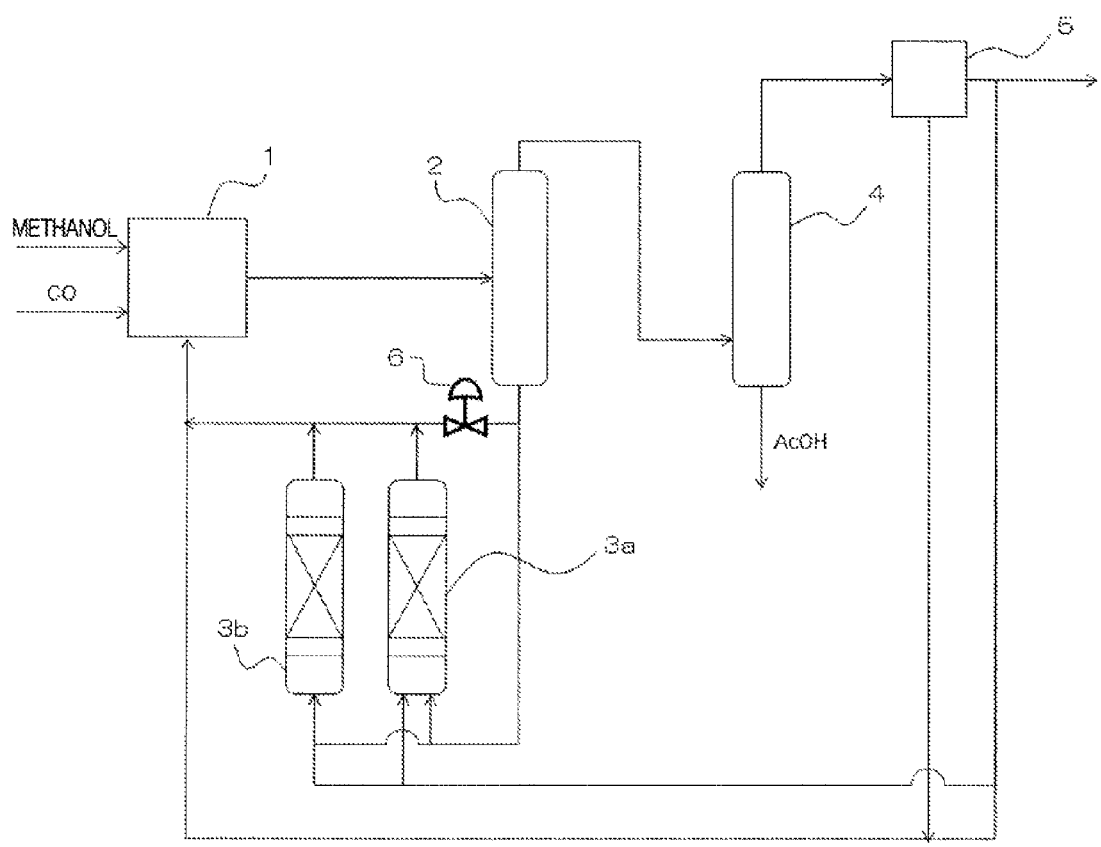
FIG. 1 is a schematic diagram illustrating one example of a carbonyl compound production process according to the present invention.

FIG. 1 is a schematic diagram illustrating one example of a carbonyl compound production process according to the present invention. The carbonyl compound production process is mainly provided with a carbonylation reactor 1 as the reaction step, a flasher 2 for performing a flash evaporation step and a light ends distillation column 4 for performing a light ends-separation step as the distillation step, a decanter 5 as a still standing step, and acidic cation-exchange resin-filled columns 3a and 3b serving as a cation exchanger.

Carbon monoxide and methanol as the carbonylation raw material are introduced to the carbonylation reactor 1. Acetic acid as a reaction solvent is circulated between the carbonylation reactor 1 and the flasher 2. A route in which a bottom product mainly including acetic acid is returned from the flasher 2 to the carbonylation reactor 1 is bifurcated on the way thereof, wherein the total amount or a part of the bottom product passes through the acidic cation-exchange resin-filled columns 3a and 3b disposed in parallel and then is returned to the carbonylation reactor 1. A gas phase fraction from the flasher 2 is flown into the light ends distillation column 4, and subjected to separation in the light ends distillation column 4. Acetic acid is separated and recovered from the lower portion of the light ends distillation column 4, and a component other than acetic acid and a part of acetic acid not recovered are distilled out from the top portion of the light ends distillation column 4. When a part of the bottom product is allowed to pass through the acidic cation-exchange resin-filled columns 3a and 3b, another part thereof is circulated to the carbonylation reactor 1 via a flow control valve 6.

A solid catalyst made of a resin carrier containing quaternized nitrogen and a noble metal complex supported on the resin carrier in an ion-exchange manner is present in the carbonylation reactor 1 with being dispersed in the liquid phase.

The resin carrier containing quaternized nitrogen according to the present invention is typically a pyridine resin, namely, a resin including in its structure a pyridine ring whose nitrogen atom can be quaternized, and representatively, for example, a copolymer of 4-vinylpyridine and divinylbenzene. The resin carrier, however, is not limited to this particular resin, and is meant to comprehensively include a resin containing basic nitrogen that can be quaternized to adsorb and support the noble metal complex. Accordingly, it is possible to use a resin including instead of the 4-vinylpyridine various basic nitrogen-containing monomers such as 2-vinylpyridine having a vinyl group at a different position, substituted vinylpyridines, for example vinylmethylpyridine, and vinylquinolines, or a resin including instead of divinylbenzene various crosslinkable monomers having two or more groups including an ethylenically unsaturated bond. Furthermore, it is also possible to use a resin including other polymerizable comonomer such as styrene and methyl acrylate in addition to the basic nitrogen-containing monomers and the crosslinkable monomers.

The degree of crosslinking of the resin carrier (expressing the content rate of the crosslinkable monomer as % by weight) is preferably 10% or more and still preferably 15 to 40%. If the degree of crosslinking is less than 10%, swelling or contraction due to the composition of the liquid phase is remarkable, and if the degree of crosslinking is too high, the content of the basic nitrogen for supporting the noble metal complex is too low. The content of the basic nitrogen in the resin may be about 2 to 10 meq/g as the basic equivalent, and is more preferably 3.5 to 6.5 meq/g. The basic nitrogen can be generally present, as the form of a free base, an acid addition salt, an N-oxide or the like, but in the present invention, they adsorb and support the noble metal complex in the state of being quaternized in an ion-exchange manner. The resin carrier is usually used in the form of a spherical particle, and the size of the particle is generally 0.01 to 2 mm, preferably 0.1 to 1 mm, and further preferably 0.25 to 0.7 mm.

The noble metal complex supported on the resin carrier refers to a complex of a noble metal that exhibits a catalytic action to the carbonylation reaction according to the present invention, the complex being adsorbed to the quaternized nitrogen of the resin carrier in an ion-exchange manner. As such a noble metal, rhodium or iridium is known, and in general rhodium is suitably used. When the resin carrier is brought into contact with a halide of rhodium or a rhodium salt such as rhodium acetate in a solution including methyl iodide under pressure of carbon monoxide (0.7 to 3 MPa), rhodium can be supported on the resin carrier. Herein, a nitrogen atom in the resin carrier is quaternized, and a rhodium complex ion produced by a reaction of a rhodium halide, methyl iodide and carbon monoxide, namely, a rhodium carbonyl complex $[Rh(CO)_2I_2]^-$ is adsorbed thereto in an ion-exchange manner, providing a solid catalyst for use in the present invention.

The carbonylation raw material as the carbonyl compound raw material for use in the method for producing a carbonyl compound of the present invention refers to one that reacts with carbon monoxide in the presence of the solid catalyst to produce a carbonyl compound. The carbonylation raw material is typically methanol, which reacts with carbon monoxide to produce acetic acid. Herein, a reaction accelerator such as methyl iodide is suitably added thereto. While this reaction is usually performed with acetic acid as a reaction solvent, the acetic acid is a reaction product and at the same time serves as a reaction solvent in this case. For example, carbon monoxide gas is blown into the reaction liquid, in which the solid catalyst is dispersed, in the carbonylation reactor 1, and methanol reacts with carbon monoxide in the presence of a rhodium complex-supported solid catalyst under conditions of a reaction temperature of about 100 to 200° C. and a reaction pressure of about 1 to 5 MPa, thereby producing acetic acid. Since methyl acetate, dimethyl ether, water and the like are produced as reaction by-products in this reaction and they are returned, together with the solvent, the reaction accelerator and the unreacted raw material, to the reaction step as residual liquids from which acetic acid is separated and recovered as a product, the liquid phase in the reaction step of the present invention is made of a mixture of all the components.

In the method for producing a carbonyl compound of the present invention, the reaction product liquid produced in the reaction step is subjected to a separation operation in the next distillation step, the produced acetic acid is separated and recovered as a product, and with respect to the residual liquid other than the product, a part thereof is returned to the reaction step and the residue thereof is transferred to the still standing step. For example, the reaction liquid is taken out from the carbonylation reactor 1 as the reaction step via a screen or the like, and then flown into the flasher 2. In the distillation step, a procedure is adopted in which a part of the reaction liquid is first gasified in the flasher 2 to separate the reaction liquid to a gas phase and a liquid phase (flash evaporation step), and thereafter the gas phase fraction is guided from the upper portion of the flasher 2 to the light ends distillation column 4 and acetic acid is separated and recovered from the lower portion of the light ends distillation column 4 (light ends separation step). The reason why such a procedure is adopted is that, while the reaction product liquid is a mixture of various components as described above and acetic acid is a component having a small volatility among them, a lower-volatile (or non-volatile) impurity is actually incorporated to the reaction product liquid and thus acetic acid may not be recovered from the bottom product as a product. The flasher 2 and the light ends distillation column 4 can be each configured as a different column as illustrated in FIG. 1, or can be provided on the bottom portion and the upper portion of a single column in an integrated manner. Since the carbonylation reaction is generally an exothermic reaction, a part of the reaction liquid is gasified in the flasher 2 to thereby exert the effect of cooling a liquid phase fraction to be returned to the reaction step, and the heated reaction product liquid is introduced to the flasher 2 to enable to function as an evaporator for the light ends distillation column 4.

The gas phase fraction is separated in the light ends distillation column 4. A part of acetic acid having the smallest volatility among the components constituting the gas phase fraction is allowed to pool in the lower portion of the light ends distillation column 4 to enable all of other gas phase components to be included in a column top distillate. Acetic acid is taken out from the lower portion of the light ends distillation column 4, subjected to a necessary purification treatment, and then separated and recovered as a product. On the other hand, a liquid flown out from the column top is introduced to the decanter 5.

While a part not gasified in the flasher 2 pools as the liquid phase fraction in the bottom portion of the flasher 2 and is returned to the carbonylation reactor 1 for performing the reaction step as the bottom product (namely, the liquid phase fraction from the flasher 2) from the distillation step, the total amount or a part of the bottom product passes through the acidic cation-exchange resin-filled columns 3a and 3b serving as a cation exchanger on the way of the returning route. The bottom product mainly includes acetic acid as the solvent, but, when a basic nitrogen-containing molecule such as a pyridine ring is eluted by decomposition from the resin carrier forming the solid catalyst, in the carbonylation reactor, the bottom product also includes such a molecule component. Therefore, before the bottom product is returned to the reaction step, the bottom product is brought into contact with the acidic cation-exchange resin-filled columns 3a and 3b to allow the nitrogen compound included in the bottom product, to be adsorbed to the acidic cation-exchange resin-filled columns 3a and 3b for removal, and thus the nitrogen compound is not present in the reaction liquid in a high concentration.

The acidic cation-exchange resin for use in the acidic cation-exchange resin-filled columns 3a and 3b in the present invention is not particularly limited, but a porous resin with pores having a pore size of 20 nm or more (macroporous type) is preferable. In addition, while the acidic cation-exchange resin includes a strongly acidic resin having a sulfonic acid type ion exchange group and a weakly acidic resin having a carboxylic acid type ion exchange group, a strongly acidic resin is preferable in terms of selective adsorptivity for the basic nitrogen-containing molecule. As such a resin, for example, Amberlyst 15 produced by Rohm & Haas is commercially available and can be suitably used.

As described above, when the bottom product from the distillation step is brought into contact with the acidic cation-exchange resin-filled columns 3a and 3b to allow the nitrogen compound included in the bottom product to be adsorbed for removal, an oligomer having two or more pyridine groups may also be adsorbed to the acidic cation-exchange resin-filled columns 3a and 3b in a slight amount, and such an oligomer may capture the noble metal complex in the bottom product to allow the noble metal complex to be gradually accumulated in the acidic cation-exchange resin-filled columns 3a and 3b. As a result, the amount of the noble metal complex possessed in the carbonylation reactor 1 may be reduced, resulting in the reduction in carbonylation reaction rate involving in the production of the carbonyl compound.

Therefore, a liquid having a higher moisture concentration than the bottom product is brought into contact with the acidic cation-exchange resin-filled columns 3a and 3b that have had contact with the bottom product returning from the distillation step to the reaction step, to allow the noble metal complex accumulated in the acidic cation-exchange resin-filled columns 3a and 3b to be extracted. The liquid including the noble metal complex extracted from the acidic cation-exchange resin-filled columns 3a and 3b can be introduced to the reaction step to return the noble metal complex to the carbonylation reactor 1. The noble metal complex returned to the carbonylation reactor 1 is supported on the solid catalyst again. The noble metal complex is thus recovered in the reaction step to further suppress the reduction in the amount of the noble metal complex in the reaction step, and suppress the reduction in carbonylation reaction rate. Herein, the moisture concentration in the liquid for use in extraction of the noble metal complex in the present invention may be higher than the moisture concentration in the bottom product that is being returned from the distillation step to the reaction step, and may be at least 10% by weight or more, preferably 30% by weight, more preferably 50% by weight, and further preferably 60% by weight or more.

With respect to the mechanism where, after the bottom product that is being returned from the distillation step to the reaction step is brought into contact with the acidic cation-exchange resin-filled columns 3a and 3b, the liquid having a higher moisture concentration than the bottom product is brought into contact with the acidic cation-exchange resin-filled columns 3a and 3b to thereby allow the noble metal complex accumulated in the acidic cation-exchange resin-filled columns 3a and 3b to be extracted, the present inventors presume as follows. Herein, the "after the bottom product is brought into contact with the acidic cation-exchange resin-filled column" means various modes including not only a case where flowing of the bottom product is stopped and switched to flowing of the liquid having a high moisture concentration, but also a case where flowing of the bottom product is continued or the flow rate of the bottom product is reduced and the liquid having a high moisture concentration is mixed with the bottom product to allow the resultant to pass through as a mixed flow.

When the noble metal is rhodium, the rhodium complex ion $[Rh(CO)_2I_2]^-$ and the quaternized pyridine ring in the solid catalyst are adsorbed in an ion-exchange manner, and the ion-exchange equilibrium highly shifts to the adsorption side. In addition, the equilibrium highly depends on the moisture concentration in the reaction field. For example, the moisture concentration and the rhodium concentration in the reaction product liquid around the outlet of the reaction step upon introduction from the reaction step to the distillation step are 3 to 7% by weight and 1 to 2 ppm, respectively. On the other hand, it is considered that the rhodium complex ion $[Rh(CO)_2I_2]^-$ and the quaternized pyridine ring of the oligomer captured by the acidic cation-exchange resin-filled columns 3a and 3b are also adsorbed in the same manner. The reaction product liquid introduced from the reaction step to the distillation step, however, is concentrated in the distillation step and the moisture concentration is also thereby reduced. Therefore, even a slight amount of the oligomer adsorbed to the acidic cation-exchange resin-filled columns 3a and 3b may capture a trace amount of the rhodium complex ion $[Rh(CO)_2I_2]^-$ included in the bottom product. The presence ratio of the quaternized pyridine ring to the rhodium complex captured by the acidic cation-exchange resin-filled columns 3a and 3b is under a solid-liquid equilibrium, and the equilibrium is controlled by the moisture concentration in the reaction field. Therefore, when the liquid having a high moisture concentration is fed to the acidic cation-exchange resin-filled columns 3a and 3b, the ion-exchange equilibrium can shift to the desorption side to thereby desorb the rhodium complex from the acidic cation-exchange resin-filled columns 3a and 3b.

The liquid having a high moisture concentration is not particularly limited as long as it is a liquid whose moisture concentration is higher than the moisture concentration in the bottom product that is being returned from the distillation step to the reaction step. For example, such a liquid may be a liquid phase discharged from a certain step in the production process of the present invention, or a liquid phase introduced from the outside of the production process of the present invention.

One example of the method for extracting the rhodium complex from the acidic cation-exchange resin-filled columns 3a and 3d is preferably configured as follows. The liquid flown out from the column top of the light ends distillation column 4, mainly including methyl iodide, methyl acetate and water, is introduced to the decanter 5 after acetic acid is separated therefrom in the distillation step. The liquid flown out therefrom is left to still stand in the decanter 5 and thus methyl iodide included in the liquid flown out therefrom is separated as a heavy oil phase, providing an aqueous phase having a moisture concentration of up to about 60% by weight. The separated methyl iodide is returned to the carbonylation reactor 1. In addition, the aqueous phase from which methyl iodide is separated and removed is bifurcated while it is being returned from the decanter 5 to the carbonylation reactor 1, and a part of the aqueous phase passes through the acidic cation-exchange resin-filled columns 3a and 3b and then is returned to the carbonylation reactor 1. That is, the aqueous phase having a higher moisture concentration than the bottom product is brought into contact with the acidic cation-exchange resin-filled columns 3a and 3b to which the nitrogen compound is adsorbed, thereby enabling to effectively extract the rhodium complex accumulated in the acidic cation-exchange resin-filled columns 3a and 3b. The aqueous phase including the extracted rhodium complex is returned to the reaction step, and thus the rhodium complex is recovered in the carbonylation reactor 1, the reduction in the amount of the rhodium complex in the carbonylation reactor 1 is suppressed, and the reduction in carbonylation reaction rate is suppressed. Herein, methyl acetate and water included in the aqueous phase are components useful for the carbonylation reaction, and it is thus preferable for the method for producing a carbonyl compound of the present invention to return to the reaction step the aqueous phase after feeding to the acidic cation-exchange resin-filled columns 3a and 3b.

The apparatus for bringing the bottom product and the above liquid into contact with the acidic cation-exchange resin-filled columns 3a and 3b is not particularly limited, but is preferably a fixed bed system in which the bottom product and the liquid are flown to the acidic cation-exchange resin-filled columns 3a and 3b, in order to ensure that the nitrogen compound and the noble metal complex are adsorbed and extracted. In this case, a plurality of the acidic cation-exchange resin-filled columns 3a and 3b are provided in parallel as illustrated in FIG. 1 and adsorption (adsorption of the nitrogen compound included in the bottom product to the acidic cation-exchange resin-filled column) and recycling (extraction of the noble metal complex captured by the nitrogen compound adsorbed to the acidic cation-exchange resin-filled column) are performed in a circulation manner, thereby enabling to continuously treat the bottom product to continuously produce a carbonyl compound for a long period. The feeding temperature of the bottom product and the liquid to the acidic cation-exchange resin-filled columns 3a and 3b during the adsorption/extraction operation and the retention time thereof are preferably about 30 to 100° C. and about 0.5 to 5 hours, respectively. Herein, the method for introducing the bottom product and the liquid to the acidic cation-exchange resin-filled columns 3a and 3b may be an upflow or downflow type.

EXAMPLES

Hereinafter, the present invention is described with reference to Examples for further understanding of the present invention, but is not limited to Examples at all.

As an acidic cation-exchange resin-filled column, a cation-exchange filled column obtained by filling a column made of double jacket glass, having a diameter of 10 mm and a length of 300 mm, with 16.4 ml of Amberlyst 15JWET (produced by The Dow Chemical Company) was used.

Accumulation of Nitrogen Compound and Rh

A liquid (decomposition rate: about 20%, nitrogen compound concentration: about 500 ppm) obtained by accelerated thermal decomposition of a solid catalyst (one obtained by supporting a rhodium complex on a vinylpyridine resin in the presence of carbon monoxide and methyl iodide (by the production method and the catalyzation method of the resin carrier described in Japanese Patent Application Laid-Open No. 2012-081440)) was used to prepare a first simulant liquid corresponding to a liquid phase distillate of a flasher. The moisture concentration in the first simulant liquid was here 4.9% by weight.

The prepared first simulant liquid was charged to a glass autoclave, and subjected to a CO treatment under stirring. An object of this treatment is to reconvert, to a rhodium complex, rhodium iodide produced by the contact with air during the thermal decomposition operation.

Then, a metering pump was used to feed the first simulant liquid to an acidic cation-exchange resin-filled column warmed at 40° C. at about 90 ml/h for 2 hours, allowing a nitrogen compound and Rh in the first simulant liquid to be accumulated in the acidic cation-exchange resin-filled column.

Recovery (Extraction) of Rh

A second simulant liquid corresponding to an aqueous phase to be returned from a decanter to a carbonylation reactor was fed to the acidic cation-exchange resin-filled column (40° C.), in which the nitrogen compound and Rh were accumulated, at about 40 ml/h for 5 hours. The moisture concentration in the second simulant liquid was here 64.6% by weight.

Figure 2:
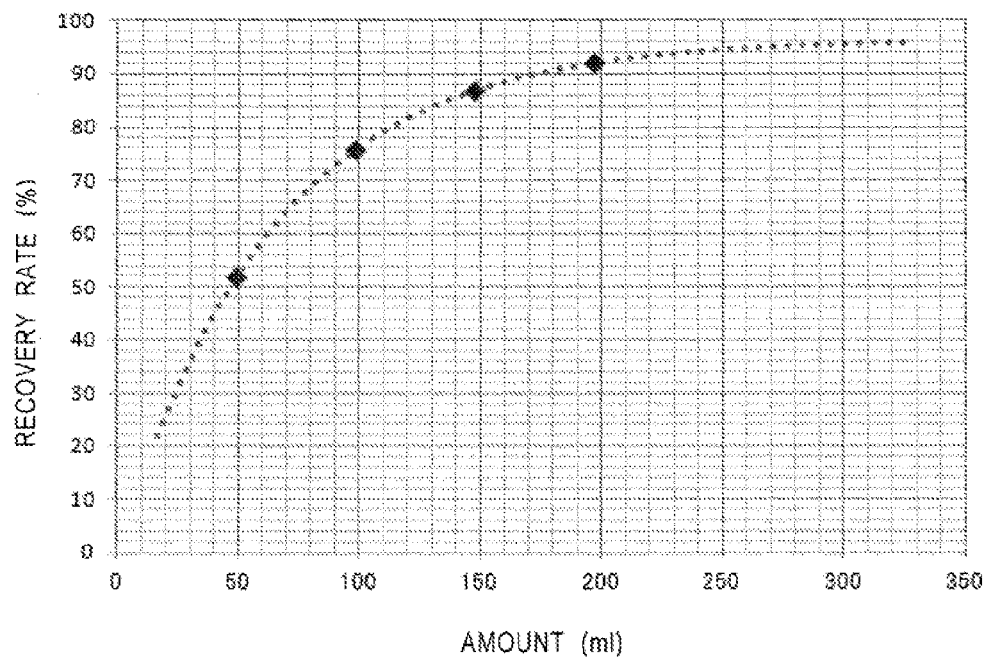
FIG. 2 is a graph showing a relationship between the amount of a second simulant liquid fed to an acidic cation-exchange resin-filled column and the recovery rate of Rh accumulated in the acidic cation-exchange resin-filled column, in Examples of the present invention.
Figure 3:
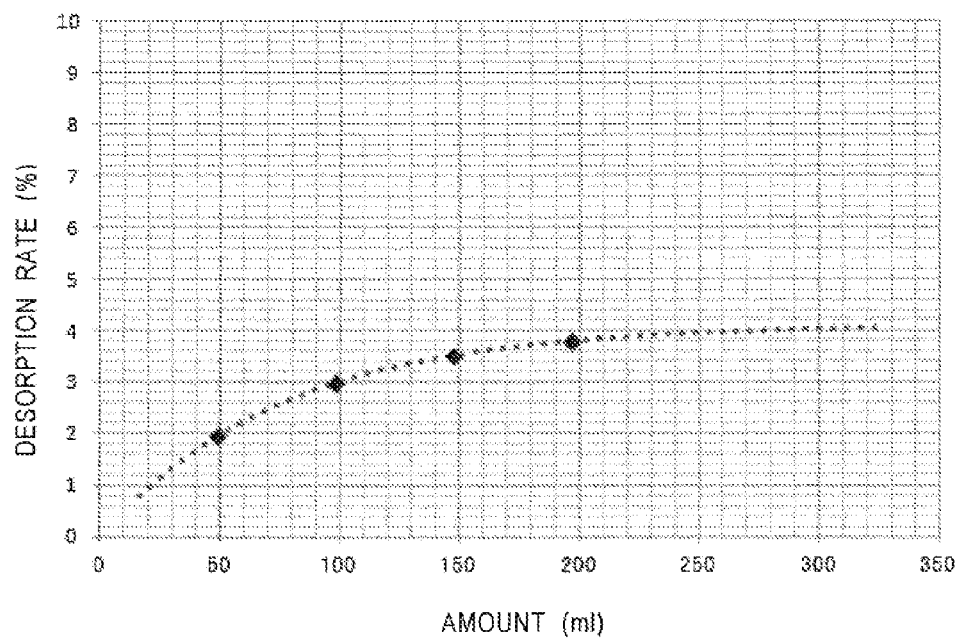
FIG. 3 is a graph showing a relationship between the amount of a second simulant liquid fed to an acidic cation-exchange resin-filled column and the desorption rate of a nitrogen compound adsorbed to the acidic cation-exchange resin-filled column, in Examples of the present invention.

The second simulant liquid after feeding was collected every 50 ml of the second simulant liquid that had fed to the acidic cation-exchange resin-filled column to measure the nitrogen compound concentration and the Rh concentration. A relationship between the amount of the fed second simulant liquid and the recovery rate of Rh accumulated in the acidic cation-exchange resin-filled column is shown in FIG. 2, and a relationship between the amount of the fed second simulant liquid and the desorption rate of the nitrogen compound adsorbed to the acidic cation-exchange resin-filled column is shown in FIG. 3.

When the amount of the fed second simulant liquid reached 200 ml (corresponding to about 12 Bed Volume), about 92% of Rh accumulated in the acidic cation-exchange resin-filled column was recovered. Herein, when the amount is 300 ml (corresponding to about 18 Bed Volume), it is expected that about 96% of Rh accumulated in the acidic cation-exchange resin-filled column can be recovered. On the contrary, the desorption rate of the nitrogen compound adsorbed to the acidic cation-exchange resin-filled column is up to about 4%.

It has been found that a liquid phase discharged from a certain step in the production process, for example, a liquid phase returned from a decanter to a carbonylation reactor is used to wash an acidic cation-exchange resin-filled column, thereby enabling to effectively recover the accumulated noble metal complex together with the oligomer.

This application claims the benefit of Japanese Patent Application No. 2013-119046, filed Jun. 5, 2013, which is hereby incorporated by reference herein in its entirety.

REFERENCE SIGNS LIST 1 carbonylation reactor
2 flasher
3a, 3b acidic cation-exchange resin-filled column
4 light ends distillation column
5 decanter
6 flow control valve

The invention claimed is:

1. A method for producing a carbonyl compound, comprising:
    a reaction step of reacting a carbonylation raw material with carbon monoxide in a liquid phase including a solid catalyst having a noble metal complex supported on a resin carrier containing quaternized nitrogen to produce a carbonyl compound;
    a distillation step of distilling a reaction product liquid from the reaction step to recover a gas phase distillate including the carbonyl compound; and
    a circulation step of circulating a bottom product from the distillation step to the reaction step,
    wherein, after at least a part of the bottom product is brought into contact with an acidic cation-exchange resin to remove a nitrogen compound included in the bottom product, a liquid having a higher moisture concentration than the bottom product is brought into contact with the acidic cation-exchange resin to extract a noble metal complex captured by an oligomer adsorbed to the acidic cation-exchange resin, and the extracted noble metal complex is returned to the reaction step.

2. The method for producing a carbonyl compound according to claim 1, wherein a moisture concentration in the liquid is at least 10% by weight or more.

3. The method for producing a carbonyl compound according to claim 1, wherein the distillation step includes a flash evaporation step and a light ends separation step.

4. The method for producing a carbonyl compound according to claim 3, wherein the liquid is an aqueous phase obtained by separating at least a part of methyl iodide included in a liquid flown out from a column top of a light ends distillation column by a decanter.

5. The method for producing a carbonyl compound according to claim 1, wherein the resin carrier containing quaternized nitrogen is made of a pyridine resin.

6. The method for producing a carbonyl compound according to claim 1, wherein the noble metal complex is a complex of rhodium.

7. The method for producing a carbonyl compound according to claim 6, wherein the complex of rhodium is $[Rh(CO)_2I_2]^-$.

8. The method for producing a carbonyl compound according to claim 1, wherein in the reaction step, acetic acid is used as a solvent.

9. The method for producing a carbonyl compound according to claim 1, wherein the acidic cation-exchange resin is a strongly acidic resin.

* * * * *